United States Patent
Ben Ayed et al.

(10) Patent No.: US 9,538,920 B2
(45) Date of Patent: Jan. 10, 2017

(54) STANDALONE ANNOTATIONS OF AXIAL-VIEW SPINE IMAGES

(71) Applicant: GENERAL ELECTRIC COMPANY, Schenectady, NY (US)

(72) Inventors: Ismail Ben Ayed, London (CA); Brandon Miles, Richmond (CA); Gregory Garvin, London (CA)

(73) Assignees: London Health Sciences Centre Research Inc., London (CA); General Electric Company, Schenectady, NY (US)

( * ) Notice: Subject to any disclaimer, the term of this patent is extended or adjusted under 35 U.S.C. 154(b) by 178 days.

(21) Appl. No.: 14/273,846

(22) Filed: May 9, 2014

(65) Prior Publication Data

US 2015/0325018 A1    Nov. 12, 2015

(51) Int. Cl.
*G06K 9/00* (2006.01)
*A61B 5/00* (2006.01)
*G06T 7/00* (2006.01)
*G06K 9/62* (2006.01)
*A61B 6/03* (2006.01)
*A61B 6/00* (2006.01)

(52) U.S. Cl.
CPC .......... *A61B 5/0033* (2013.01); *G06K 9/6215* (2013.01); *G06K 9/6277* (2013.01); *G06T 7/0012* (2013.01); *G06T 7/0081* (2013.01); *A61B 6/032* (2013.01); *A61B 6/468* (2013.01); *A61B 6/505* (2013.01); *A61B 6/5211* (2013.01); *G06T 2207/10088* (2013.01); *G06T 2207/10116* (2013.01); *G06T 2207/20076* (2013.01); *G06T 2207/20081* (2013.01); *G06T 2207/30012* (2013.01)

(58) Field of Classification Search
None
See application file for complete search history.

(56) References Cited

U.S. PATENT DOCUMENTS

| | | | | |
|---|---|---|---|---|
| 2006/0280350 A1* | 12/2006 | Conrad-Hansen | .... | G06T 7/0012 382/128 |
| 2014/0133726 A1* | 5/2014 | Garner | ................ | A61B 5/4504 382/131 |
| 2015/0036909 A1* | 2/2015 | Hladuvka | ............. | G06T 7/0081 382/131 |

* cited by examiner

*Primary Examiner* — Weiwen Yang (57) ABSTRACT

Systems, methods and computer program products to annotate axial-view spine images with the desired characteristics of not requiring additional views of the spine or cross-referencing features are provided. In one aspect, the disclosed method does not require external training from a manually-labeled data set while being applicable to different imaging modalities and acquisition protocols. In one aspect, the disclosed method achieves near real-time results using integral kernels when implemented on a Graphics Processing Unit.

10 Claims, 4 Drawing Sheets

STANDALONE ANNOTATIONS OF AXIAL-VIEW SPINE IMAGES

FIELD OF DISCLOSURE

The present disclosure relates to labeling radiology images, and more particularly to systems, methods and computer program products to label radiology images using the axial view.

BACKGROUND

The statements in this section merely provide background information related to the disclosure and may not constitute prior art.

The annotations (i.e., labels) of the vertebrae and inter-vertebral discs in axial spine Magnetic Resonance Image (MRI) images (i.e., slices) are essential for further diagnosis of various spine disorders. For instance, in MRI, annotating the axial-view slices facilitates the quantification and level-based reporting of common inter-vertebral disc displacements such as protrusion, extrusion, and bulging.

Generating labels in a manual fashion is tedious, subjective, and time-consuming especially because the number of 2D slices in a series can be very high, with up to 100 images per axial series. Furthermore, it can be difficult for radiologists to determine the identity of a particular vertebra in an axial slice of the spine, because adjacent vertebrae have very similar appearances. Even when a particular vertebra has been identified in a particular axial slice, a radiologist must remember its identity and location as they make a diagnosis from multiple axial slices in a series.

Current spine labeling algorithms focus on the sagittal view only. However, the quantification and level-based reporting of common inter-vertebral disc displacements such as protrusion, extrusion, and bulging require the radiologist to thoroughly inspect all individual axial slices while visually cross-referencing such axial slices to their corresponding position in the sagittal view. This requires labeling the sagittal view, which has at least two limitations. First, sagittal images are not always available for every patient (i.e., only the axial view may be available) while in other cases the two scans might be acquired at different time points. In such cases, when deformations between sagittal and axial images occur because of patient repositioning, cross-referencing may not be reliable. Therefore, localizing the spinal structures in different views becomes challenging (even for an experienced radiologist). Second, using a sagittal-view labeling along with the cross-reference feature allows to label not all, but only a few slices in the axial series.

Most of the current spine labeling algorithms address the above described labeling limitations through intensive external training from a manually-labeled data set. Such training aims to refine the algorithms to learn the shapes, textures and appearances of different spinal structures. This knowledge is then used within a classification or regression algorithm such as support vector machine, random forest regression or graphical models to subsequently label different spinal structures in the test image. Such algorithms work very well on data sets that closely match the training data, but require adjustment/retraining for different data sets or if the imaging modality and/or acquisitions protocol are altered (e.g., an algorithm that is trained and built for Computerized Tomography (CT) images may not perform well on Magnetic Resonance (MR) data). This impedes the use of these algorithms in routine clinical practices, where a particular disorder might be analyzed radiologically using several different imaging modalities/protocols with widely variable imaging parameters.

BRIEF SUMMARY

In view of the above, there is a need for systems, methods, and computer program products which can annotate axial spine images without the need of additional views of the spine or cross-referencing features and does not require external training from a manually-labeled data set. The above-mentioned needs are addressed by the subject matter described herein.

According to one aspect of the present disclosure, a system that allows annotations of the axial slices without the need for: 1) referring to sagittal view annotations, 2) referring to cross-reference features, and 3) requiring external training while being applicable to different imaging modalities and acquisition protocols is provided.

According to another aspect of the present disclosure, a method that allows annotations of the axial slices without the need for: 1) referring to sagittal view annotations, 2) referring to cross-reference features, and 3) requiring external training while being applicable to different imaging modalities and acquisition protocols is provided.

This summary briefly describes aspects of the subject matter described below in the Detailed Description, and is not intended to be used to limit the scope of the subject matter described in the present disclosure.

BRIEF DESCRIPTION OF THE DRAWINGS

The features and technical aspects of the system and method disclosed herein will become apparent in the following Detailed Description set forth below when taken in conjunction with the drawings in which like reference numerals indicate identical or functionally similar elements.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

I. Overview

Spinal images may be annotated and/or labeled to assist in analyzing such images and/or diagnosing various spine diseases. However, correctly annotating and/or labeling these images is sometimes difficult because, depending on the image being viewed, the number of visible vertebrae and/or disc vary. This can be especially difficult in the case of axial spine images. To overcome some of the deficiencies encountered with some known manual or automatic annotating and/or labeling methods, aspects of the present disclosure disclosed and described herein enable the stand-alone, automatic labeling of axial spine images using a comprehensive set of geometric measurements of the human spine as input parameters, (e.g., vertebra height and axial area). In addition, aspects disclosed may also annotate axial spine images without the need for: 1) referring to sagittal view annotations, 2) referring to cross-reference features, and 3) requiring external training while being applicable to different imaging modalities and acquisition protocols.

Other aspects, such as those discussed below and others as can be appreciated by one having ordinary skill in the art upon reading the enclosed description, are also possible.

II. Example System

Figure 1:
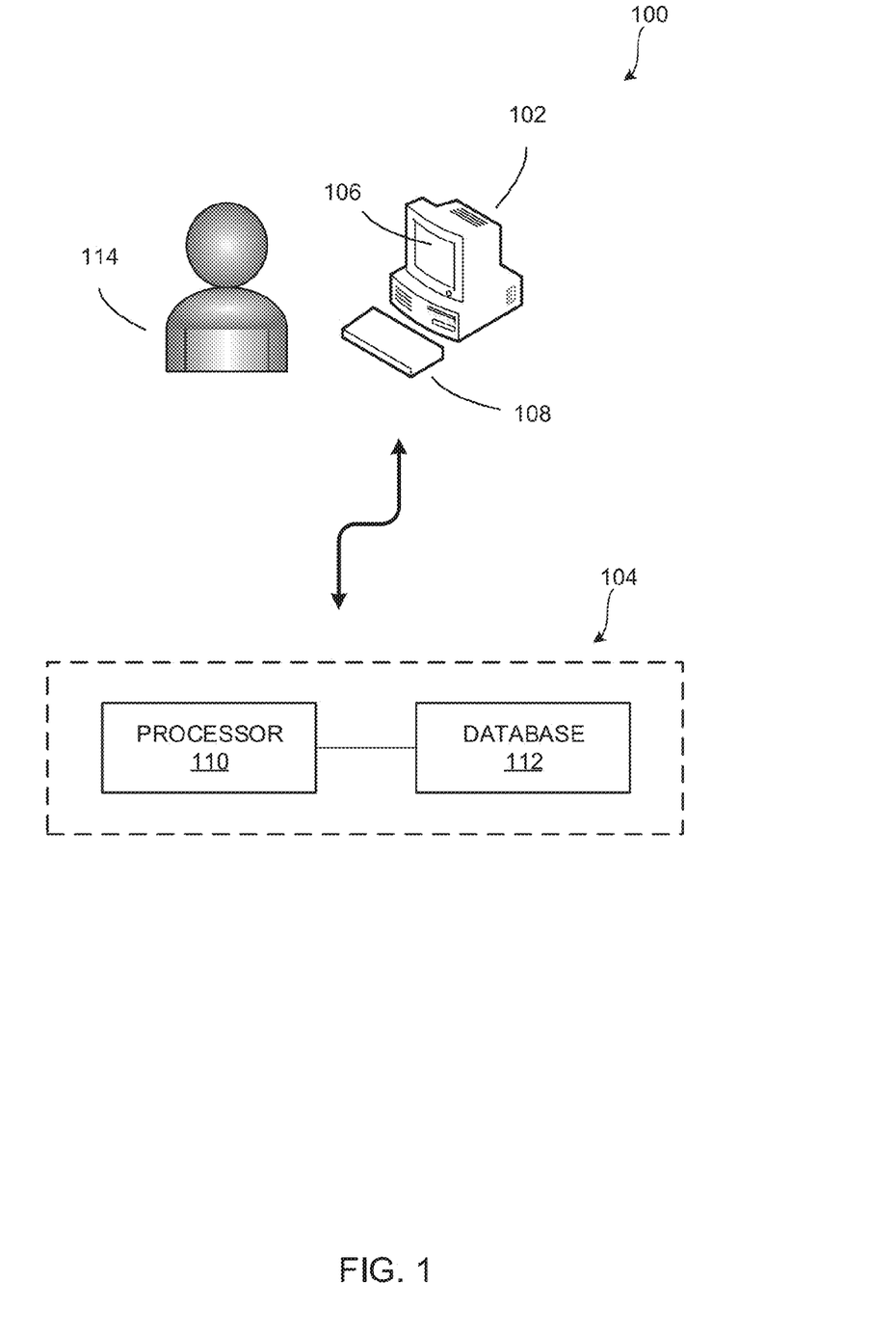
FIG. 1 shows a block diagram of an example annotation radiology image system according to one aspect of the present disclosure.

FIG. 1 depicts an example system 100 for annotating images such, as spinal images, according to one aspect of the present disclosure. System 100 includes a computer 102 and an annotator 104 communicatively coupled to computer 102. In this example, computer 102 includes a user interface 106 and a data input (e.g., a keyboard, mouse, microphone, etc.) 108 and annotator 104 includes a processor 110 and a database 112.

In certain aspects, user interface 106 displays data such as images (e.g., spinal images, radiology images, etc.) and/or annotated images received from annotator 104. In certain aspects, user interface 106 receives commands and/or input from a user 114 via data input 108. In aspects where system 100 is used to annotate spinal images, user interface 106 displays a spinal image(s) and/or annotated spinal image(s) and user 114 provides an initial input identifying, for example, a location of a vertebra on the spinal image(s) and/or provides subsequent input identifying the location of a vertebra based on offline, a priori external training.

Figure 2:
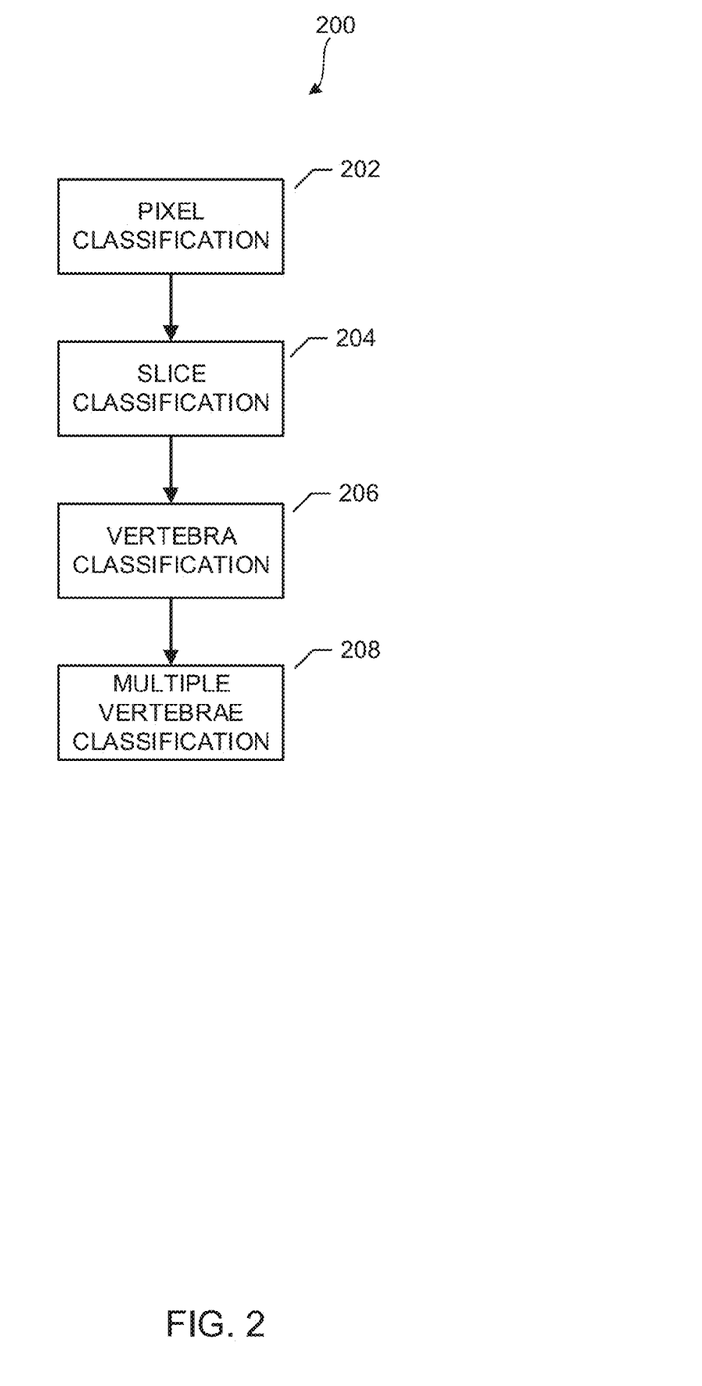
FIG. 2 shows a flow diagram illustrating an example method of the classification hierarchy of operating the system of FIG. 1, according to one aspect of the present disclosure.

FIG. 2 illustrates a flow diagram of annotator 104 according to one aspect of the present disclosure. While annotator 104 may generate annotations using any suitable labeling algorithm, in some aspects, annotator 104 generates annotations based on a hierarchy of feature levels, where pixel classifications 202 via non-linear probability product kernels (PPK) are followed by classifications of 2D slices 204, 3D single vertebra structures 206, and 3D multiple vertebra structures 208. In some aspects, annotator 104 embeds robust geometric priors based on anatomical measurements that are well known to those skilled in the relevant art(s) (e.g., vertebra height and axial area).

In certain aspects, efficient pixel-level classifications 202 via integral kernels are used. In one aspect, a non-linear classifier is used, which determines whether the neighborhood of each pixel p matches a target distribution denoted $P^L$. Certain aspects can use offline, external training to set an initial vertebrae pixel location to provide initial classifications. In another aspect, user 114 can select a single point $p_0=(x_0, y_0)$ within the vertebral region in a single 2D axial slice in the series via data input 108 to provide initial training. Then, the target distribution $P^L$ is learned from a window of size w×h centered at $p_0$.

In one aspect, neighborhood distributions contain contextual information, which provides much richer inputs to the classifier than individual-pixel intensities. For example, let $D_j:\Omega \subset \mathbb{R}^2 \to \mathbb{R}$, $j \in [1 \ldots N]$, be a set of input images, which correspond to the axial slices of a given spine series. $\Omega$ is the image domain and N is the number of slices in the series. For each $D \in \{D_j, j=1 \ldots N\}$ and each pixel $p:(x, y) \in \Omega$, a non-linear kernel based classifier is created using the following:

$$\text{sign}(\phi)(P_{p,W,D}, P^L) - \rho) \qquad \text{Equation 1:}$$

where $P^L$, is the a priori learned distribution, $\rho$ is a constant and $P_{p,W,D}$ is the kernel density estimate (KDE) of the distribution of the data D within window W centered at pixel $p=(x, y) \in \Omega$:

$$P_{p,W,D} = \frac{\sum_{p \in W} k_z^D(p)}{|W|} \forall z \in Z.$$

[W] is the number of pixels within W and Z is a finite set of bins encoding the space of image variables. $k_z^D$ is a Dirac kernel: $k_z^D = \delta(z-D(p))$, where $\delta(t)=1$ if $t=0$, and 0 elsewhere. In certain aspects, a Gaussian kernel can be used instead of $\delta$. $\phi$ is a probability product kernel which measures the degree of similarity between two distributions:

$$\phi(P_{p,W,D}, P^L) = \sum_{z \in Z} [P_{p,W,D}(z) P^L(z)]^{\gamma}, \gamma \in [0,1] \qquad \text{Equation 2:}$$

In certain aspects, an efficient method to determine kernel density estimates and PPK evaluations for large images and arbitrary window sizes via integral kernels can be computed as integral images as follows:

Given an image $\mathcal{D}$, the corresponding integral image $\mathfrak{I}^{\mathcal{D}}$ is defined as the sum of all pixel intensities to the left and above the current pixel: $\mathfrak{I}^{\mathcal{D}}(x, y) = \sum_{u \leq x} \sum_{v \leq y} D(u, v)$. The sum of intensities of all pixels within an arbitrary rectangular can be computed from $\mathfrak{I}^{\mathcal{D}}$ using only the corners of the rectangle:

$$\sum_{u=x_1}^{x_2} \sum_{v=y_1}^{y_2} \mathcal{D}(u,v) = \mathfrak{I}^{\mathcal{D}}(x_1, y_1) + \mathfrak{I}^{\mathcal{D}}(x_2, y_2) - \mathfrak{I}^{\mathcal{D}}(x_1, y_2) - \mathfrak{I}^{\mathcal{D}}(x_2, y_1) \qquad \text{Equation 3:}$$

where $(x_1, y_1)$ are the coordinates of the upper left corner of the rectangle and $(x_2, y_2)$ are those of the lower right corner.

In certain aspects, integral images can be treated as integral kernels to enable the computation of the PPK in Equation 2 as follows:

For each slice $\mathcal{D}$ a set of separate kernel images defined over $\Omega$: $k_1^{\mathcal{D}}, k_2^{\mathcal{D}}, \ldots, k_z^{\mathcal{D}}, z \in \mathcal{Z}$, (with $k_z^{\mathcal{D}}$ the Dirac kernel defined earlier) are created. Next, an integral kernel image is computed based on each $k_z$: $\mathfrak{I}_z^{\mathcal{D}}(x, y) = \sum_{u \leq x} \sum_{v \leq y} k_z^{\mathcal{D}}(u, v)$. $P_{p,W,\mathcal{D}}$ can be computed from the integral kernel images using five operations for each $p=(x, y) \in \Omega$:

$$P_{p,\mathcal{W},\mathcal{D}}(z) = \frac{\mathcal{I}^{\mathcal{D}}(x_1, y_1) + \mathcal{I}^{\mathcal{D}}(x_2, y_2) - \mathcal{I}^{\mathcal{D}}(x_1, y_2) - \mathcal{I}^{\mathcal{D}}(x_2, y_1)}{(x_2 - x_1 + 1)(y_2 - y_1 + 1)} \quad \text{Equation 4}$$

where $$x_1 = x - \frac{w}{2}, x_2 = x + \frac{w}{2}, y_1 = y - \frac{h}{2}, y_2 = y - \frac{h}{2},$$

where with w and h being the width and height of $\mathcal{W}$.

In certain aspects, 2D slice-level features 204 are derived from the area of pixels classified as vertebra in a given 2D slice and from geometric priors. Vertebra pixels are grouped into sets of 4-connected regions: $S^i$, i=1, 2, . . . . These regions are then filtered, building a set S as follows: $S=\{S^i | \text{area}(S^i) > A_{min} \text{ and } \|c_i, p_0\| < d_{max}\}$, where $A_{min}$ and $d_{max}$ are pre-specified geometric priors, which for example, can be defined so as to reflect human spine measurements that are well known in the clinical literature. If $S \neq \emptyset$, the area of the largest region in S is used as a 2D slice-level feature for the next step. Otherwise, a value of 0 is assigned to this feature. This feature is denoted as $A_k$ for slice $\mathcal{D}_k$.

In certain aspects, 3D single-vertebra classifications 206 are identified. An input set of adjacent slices $\mathcal{D}_k$, $k \subset [1, N]$, in the neighborhood of a vertebrae are used. These slices are all the slices within a geometric prior height $H_S$, either centered on the initial point or starting at the uppermost (or lowermost) slice of a previously identified vertebra. The slices are then classified (labeled) as either being vertebra or intervertebral disk. The input of this step uses the 2D slice-level feature computed at the previous step ($A_k$). A one-dimensional smoothing filter is then applied to the features of the adjacent slices $A_k^2 = A_k * K$, where $A_k^s$ is the smoothed data and K is a one-dimensional convolution kernel. A slice is classified as vertebra if $A_k^s > t_{area}$, where $t_{area}$ is a threshold given by $t_{area} = c_a \mu_{area}$, with $c_a$ a user defined factor, for example, and $\mu_{area}$ the average of areas $A_k^s$. If the set of adjacent slices classified as vertebrae results in a vertebral height larger than a geometric prior $H_{min}$, then the 3D set of adjacent slices is classified as vertebra. In certain aspects, the geometric priors $H_S$ and $H_{min}$ can be defined from well-known anatomical measurements from the literature.

In certain aspects, an iterative model using 3D multiple vertebrae classification 208 updating is employed to improve classification accuracy. Using the previously found vertebra, the distribution $P^L$ and search region are updated as necessary for finding the next vertebra. The classification or labeling then proceeds in both vertical directions of the spine. For the first vertebra, the initial search height, which is denoted as $H_S^0$ can be defined to be twice the height of a vertebra (which may be obtained from the literature, for example), and centered at the input point, for example. For finding subsequent vertebrae, the search range $H_S$ can begin at the boundary of the previous vertebra and extends for the height of a vertebra plus two inter-vertebral disc spaces (which may also be obtained from the literature), for example.

III. Example Method

Figure 3:
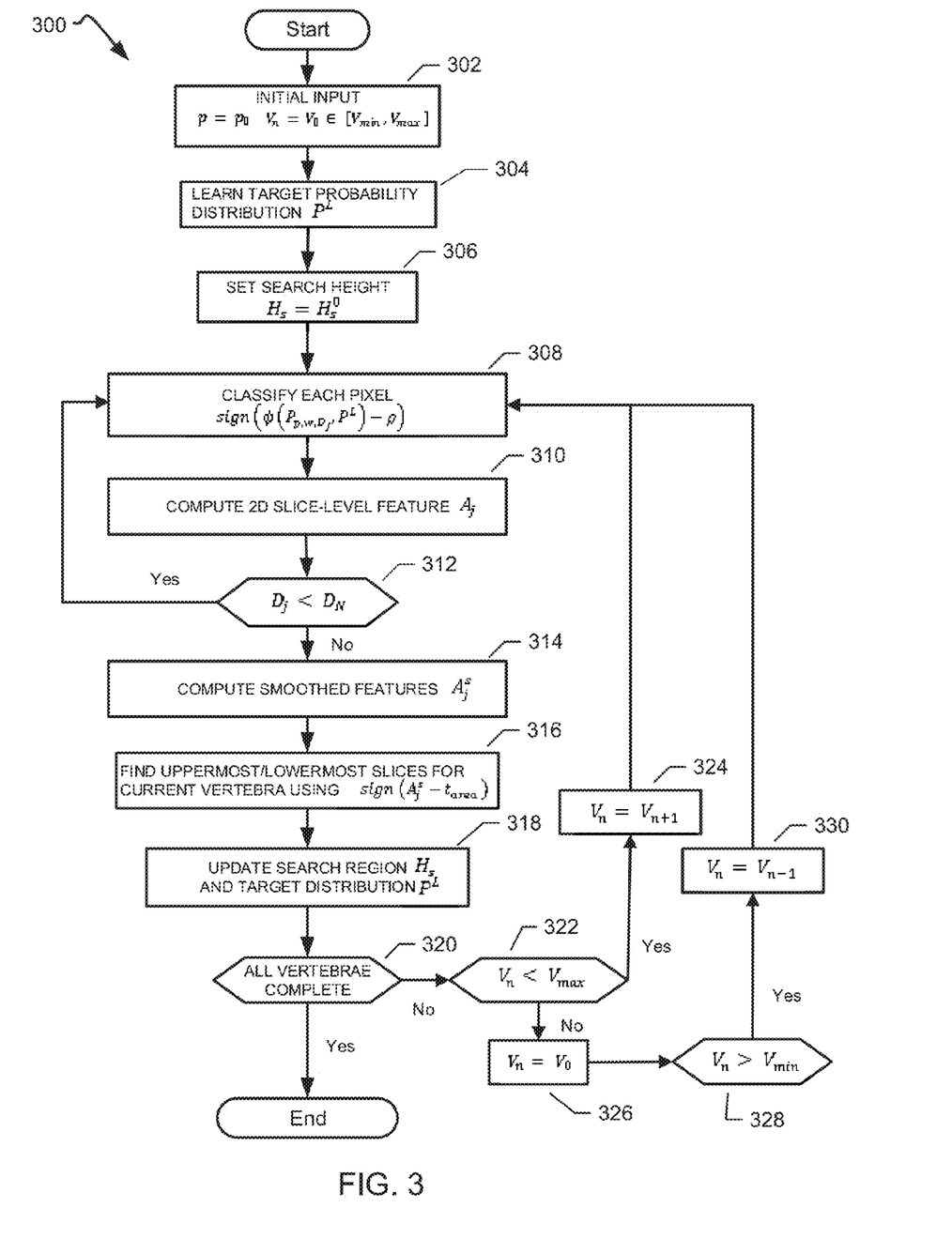
FIG. 3 shows a flow diagram illustrating implementing an example method of operating the system of FIG. 1, according to one aspect of the present disclosure.

A flowchart representative of example machine readable instructions for implementing the axial image annotation process 300 of the example system 100 is shown in FIG. 3. In these examples, the machine readable instructions comprise a program for execution by a processor such as processor 412 shown in the example processor platform 400 discussed below in connection with FIG. 4. The program can be embodied in software stored on a tangible computer readable storage medium such as a CD-ROM, a floppy disk, a hard drive, a digital versatile disk (DVD), a BLU-RAY™ disk, or a memory associated with processor 412, but the entire program and/or parts thereof could alternatively be executed by a device other than processor 412 and/or embodied in firmware or dedicated hardware. Further, although the example program is described with reference to the flowchart illustrated in FIG. 3, many other methods of implementing the example annotator can alternatively be used. For example, the order of execution of the blocks can be changed, and/or some of the blocks described can be changed, eliminated, or combined.

As mentioned above, process 300 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably.

Additionally or alternatively, process 300 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

Process 300 begins at block 302 where computer 102 receives, via data input 108, initial input on a spine image displayed at user interface 106 and/or stored in database 112 (block 302). In certain aspects of the present disclosure, to provide the initial training, the initial input is associated with a user 114 clicking on a point $p = (x_0, y_0)$ within the vertebral region in a single 2D axial slice of the spinal image series. In certain aspects, the initial training input is provided by previous, off-line, external training from another data set.

At block 304, annotator 104 generates a target distribution $P^L$ which is learned from a window of size w×h centered at $p_0$.

At block 306, annotator 104 sets the initial search height $H_S^0$, which is defined to be twice the height of an average vertebra (as defined in the clinical literature).

For each slice $D_j$ in the set of slices within the search height $H_S$, the annotator 104 performs a pixel classification and a 2D slice classification. At block 308, the pixel classification is performed by using $\text{sign}(\phi(P_{p,W,D}, P^L)-\rho)$ to classify each pixel p via integral kernels as described above. At block 310, the slice classification is performed by computing the 2D slice-level feature $A_j$.

At block 312, annotator 104 determines if all of the slices within the search height $H_S$ have been completed. If not, the pixel and slice classification is performed on the next slice in the series.

At block 314, once all the slices have been classified at the pixel and slice levels, the vertebra classification is performed by computing the smoothed features $A_j^s$ for each $D_j$ within the search height $H_S$. In addition, at block 316, the annotator then determines the uppermost and lowermost slices for the current vertebra by using the equation $\text{sign}(A_j^2-t_{area})$.

At block 318, annotator 104 updates the vertical search height $H_S$ and target distribution $P^L$.

At block 320, annotator 104 determines if all the vertebrae have been completed. If not, at block 322, annotator 104 determines if the current vertebra being examined, $V_n$, is lower than the top-most vertebra $V_{max}$. If so, the vertebra is incremented at block 324 ($V_n=V_{n+1}$) and the process of classifying the vertebra begins again at block 308. If the vertebra $V_n$ is already at $V_{max}$ then the current vertebra being examined is reset at block 326 ($V_n=V_0$) and annotator 104 determines if the vertebra being examined is higher than the lower-most vertebra at block 328 ($V_n>V_{min}$). If so, the vertebra being examined is decremented at block 330 ($V_n=V_{n-1}$) and the process of classifying the vertebra continues at block 308.

Once annotator 104 determines that all the vertebra have been completed, annotator 104 assigns labels to the disks. In certain aspects, annotator 104 also labels the intervertebral discs in between the vertebrae. In certain aspects, the annotated spine including vertebrae and disc labels is displayed to user 114 using user interface 106 and/or saved in database 112.

IV. Computing Device

The subject matter of this description may be implemented as stand-alone system or for execution as an application capable of execution by one or more computing devices 102. The application (e.g., webpage, downloadable applet or other mobile executable) can generate the various displays or graphic/visual representations described herein as graphic user interfaces (GUIs) or other visual illustrations, which may be generated as webpages or the like, in a manner to facilitate interfacing (receiving input/instructions, generating graphic illustrations) with users via the computing device(s).

Memory and processor 110 as referred to herein can be stand-alone or integrally constructed as part of various programmable devices, including for example a desktop computer, tablet, mobile device or laptop computer harddrive, field-programmable gate arrays (FPGAs), application-specific integrated circuits (ASICs), application-specific standard products (ASSPs), system-on-a-chip systems (SOCs), programmable logic devices (PLDs), etc. or the like or as part of a Computing Device, and any combination thereof operable to execute the instructions associated with implementing the method of the subject matter described herein.

Computing device as referenced herein may include: a mobile telephone; a computer such as a desktop or laptop type; a Personal Digital Assistant (PDA) or mobile phone; a notebook, tablet or other mobile computing device; or the like and any combination thereof.

Computer readable storage medium or computer program product as referenced herein is tangible (and alternatively as non-transitory, defined above) and may include volatile and non-volatile, removable and non-removable media for storage of electronic-formatted information such as computer readable program instructions or modules of instructions, data, etc. that may be stand-alone or as part of a computing device. Examples of computer readable storage medium or computer program products may include, but are not limited to, RAM, ROM, EEPROM, Flash memory, CD-ROM, DVD-ROM or other optical storage, magnetic cassettes, magnetic tape, magnetic disk storage or other magnetic storage devices, or any other medium which can be used to store the desired electronic format of information and which can be accessed by the processor or at least a portion of the computing device.

The terms module and component as referenced herein generally represent program code or instructions that causes specified tasks when executed on a processor. The program code can be stored in one or more computer readable mediums.

Network as referenced herein may include, but is not limited to, a wide area network (WAN); a local area network (LAN); the Internet; wired or wireless (e.g., optical, Bluetooth, radio frequency (RF)) network; a cloud-based computing infrastructure of computers, routers, servers, gateways, etc.; or any combination thereof associated therewith that allows the system or portion thereof to communicate with one or more computing devices.

The term user and/or the plural form of this term is used to generally refer to those persons capable of accessing, using, or benefiting from the present disclosure.

Figure 4:
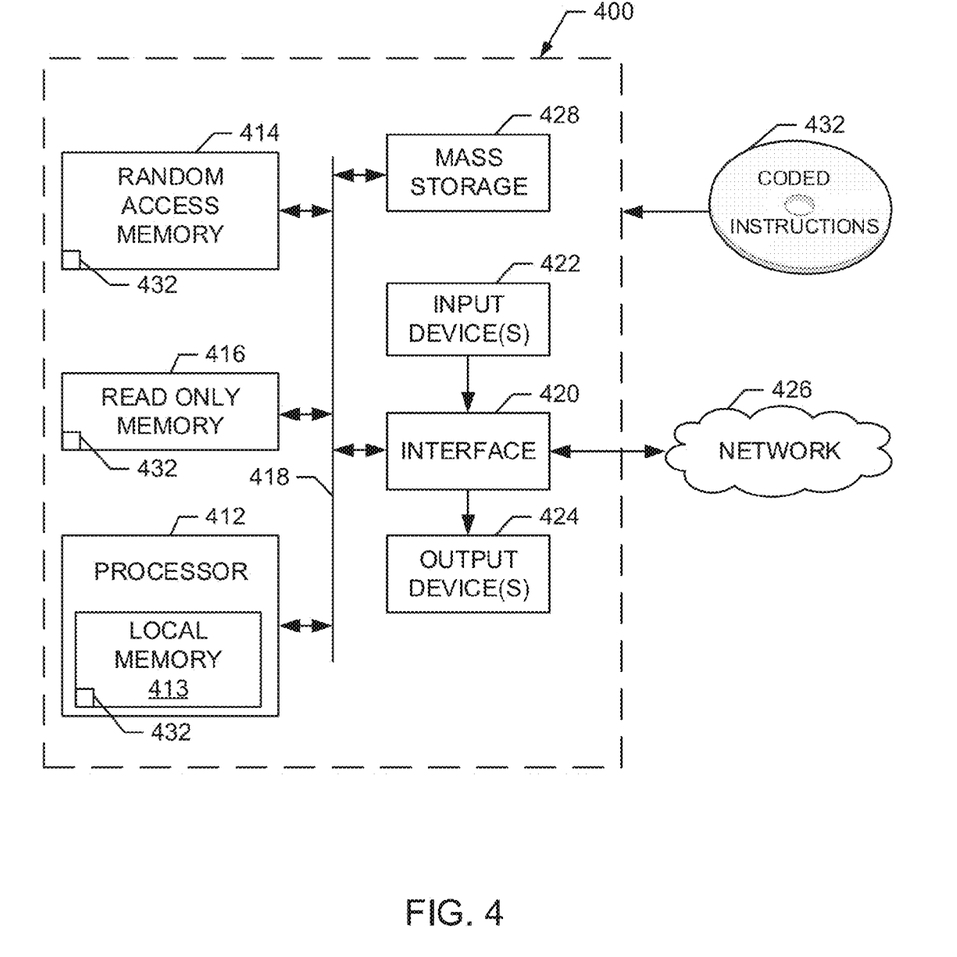
FIG. 4 shows a block diagram of an example processor system that can be used to implement the systems and methods described herein according to one aspect of the present disclosure.

FIG. 4 is a block diagram of an example processor platform 400 capable of executing process 300 for annotating images such as spinal images. Processor platform 400 may be, for example, a server, a personal computer, a mobile device (e.g., a cell phone, a smart phone, a tablet such as an IPAD™), a personal digital assistant (PDA), an Internet appliance, or any other type of computing device.

Processor platform 400 includes a processor 412. Processor 412 of the illustrated example is hardware. For example, processor 412 may be implemented by one or more integrated circuits, logic circuits, microprocessors or controllers from any desired family or manufacturer.

Processor 412 includes a local memory 413 (e.g., a cache). Processor 412 of the illustrated example is in communication with a main memory including a volatile memory 414 and a non-volatile memory 416 via a bus 418. Volatile memory 414 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 416 can be implemented by flash memory and/or any other desired type of memory device. Access to main memory 414, 416 is controlled by a memory controller.

Processor platform 400 also includes an interface circuit 420. Interface circuit 420 can be implemented by any type of interface standard, such as an Ethernet interface, a universal serial bus (USB), and/or a PCI express interface.

One or more input devices 422 are connected to the interface circuit 420. Input device(s) 422 permit(s) a user to enter data and commands into processor 412. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 424 are also connected to interface circuit 420 of the illustrated example. Output devices 424 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). Interface circuit 420 of the illustrated example, thus, typically includes a graphics driver card, a graphics driver chip or a graphics driver processor.

Interface circuit 420 of the illustrated example also includes a communication device such as a transmitter, a receiver, a transceiver, a modem and/or network interface card to facilitate exchange of data with external machines (e.g., computing devices of any kind) via a network 426 (e.g., an Ethernet connection, a digital subscriber line (DSL), a telephone line, coaxial cable, a cellular telephone system, etc.).

Processor platform 400 of the illustrated example also includes one or more mass storage devices 428 for storing software and/or data. Examples of such mass storage devices 428 include floppy disk drives, hard drive disks, compact disk drives, Blu-ray disk drives, RAID systems, and digital versatile disk (DVD) drives.

Coded instructions 432 may be stored in mass storage device 428, in volatile memory 414, in the non-volatile memory 416, and/or on a removable tangible computer readable storage medium such as a CD or DVD.

VI. Conclusion

This written description uses examples to disclose the subject matter, and to enable one skilled in the art to make and use the invention. The above disclosed methods and apparatus disclosed and described herein enable the stand-alone automatic labeling of axial spine images. From the foregoing, it will be appreciated that the above disclosed methods and apparatus provide a protocol the enables fast and user-friendly visualizations of spine annotations and/or substantially guarantees correct results in substantially all clinical scenarios. The patentable scope of the subject matter is defined by the following claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A computer-implemented method to create annotations of spine images, the method comprising:
   loading reference data comprising prior geometric measurements of the human spine;
   receiving an initial input from the selection of a point within a vertebral region in a single, two-dimensional axial-view image slice of a spinal magnetic resonance image series;
   generating a target distribution of identified pixel intensity values for said vertebral region;
   classifying each of a plurality of pixel intensity values of each said image slice of said spinal image series to determine whether such pixel intensity value belongs to vertebrae by matching each pixel context to said target distribution using a non-linear probability product integral kernel;
   wherein the context of the pixel is the kernel density estimate of intensities within a window centered at the pixel;
   classifying each of said image slices of said spinal image series by computing a two-dimensional slice-level feature which is derived from the classification of said plurality of pixels of said spinal image series and from said reference data;
   identifying three-dimensional vertebra from said two-dimensional image slice-level features; and
   generating an annotation to at least one of said two-dimensional axial image slices identifying at least one vertebra or an associated intervertebral disk.

2. The computer-implemented method of claim 1, wherein generating the annotations comprises utilizing only the axial view as input.

3. The computer-implemented method of claim 1, wherein generating the annotations is independent of external training of previously labeled data set(s).

4. The computer-implemented method of claim 1, wherein generating the annotations is independent of sagittal-view labeling along with cross-referencing features.

5. The computer-implemented method of claim 1, wherein the method further comprises:
   determining, in an offline manner, initial vertebra pixel intensity values from external data sets to provide the said target distribution.

6. A computer storage device including program instructions for execution by a computing device to perform:
   loading reference data comprising prior geometric measurements of the human spine;
   receiving an initial input from the selection of a point within a vertebral region in a single, two-dimensional axial-view image slice of a spinal magnetic resonance image series;
   generating a target distribution of identified pixel intensity values for said vertebral region;
   classifying each of a plurality of pixel intensity values of each said slice of said spinal image series to determine whether such pixel intensity value belongs to vertebrae by matching each pixel context to said target distribution using a non-linear probability product integral kernel;
   wherein the context of the pixel is the kernel density estimate of intensities within a window centered at the pixel;
   classifying each of said image slices of said spinal image series by computing a two-dimensional image slice-level feature which is derived from the classification of said plurality of pixels of said spinal image series and from said reference data;
   identifying three-dimensional vertebra from said two-dimensional image slice-level features; and
   generating an annotation to at least one of said two-dimensional axial image slices identifying at least one vertebra or an associated intervertebral disk.

7. The computer storage device of claim 6, further including program instructions for execution by said computing device to perform:
   generating the annotations uses only the axial view as input.

8. The computer storage device of claim 6, further including program instructions for execution by said computing device to perform:

generating the annotations is independent of external training of previously labeled data set(s).

9. The computer storage device of claim 6, further including program instructions for execution by said computing device to perform:

generating the annotations is independent of sagittal-view labeling along with cross-referencing features.

10. The computer storage device of claim 6, further including program instructions for execution by said computing device to perform:

determining, in an offline manner, initial vertebra pixel intensity values from external data sets to provide the said target distribution.

* * * * *